United States Patent
Masuno et al.

(10) Patent No.: US 9,890,101 B2
(45) Date of Patent: *Feb. 13, 2018

(54) METHODS OF PRODUCING PARA-XYLENE AND TEREPHTHALIC ACID

(71) Applicant: MICROMIDAS, INC., West Sacramento, CA (US)

(72) Inventors: Makoto N. Masuno, Elk Grove, CA (US); Douglas Cannon, Sacramento, CA (US); John Bissell, II, Sacramento, CA (US); Ryan L. Smith, Sacramento, CA (US); Alex B. Wood, Sacramento, CA (US); Patrick B. Smith, Midland, MI (US); Dennis A. Hucul, Midland, MI (US); Katherine Brune, West Sacramento, CA (US)

(73) Assignee: MICROMIDAS, INC., West Sacramento, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/993,833

(22) Filed: Jan. 12, 2016

(65) Prior Publication Data

US 2016/0362357 A1    Dec. 15, 2016

Related U.S. Application Data

(63) Continuation of application No. 14/345,216, filed as application No. PCT/US2012/055651 on Sep. 14, 2012, now Pat. No. 9,260,359.

(Continued)

(51) Int. Cl.
C07C 51/16    (2006.01)
C07C 2/86    (2006.01)
(Continued)

(52) U.S. Cl.
CPC .......... *C07C 51/16* (2013.01); *C07C 2/52* (2013.01); *C07C 2/862* (2013.01); *C07C 2/865* (2013.01);
(Continued)

(58) Field of Classification Search
None
See application file for complete search history.

(56) References Cited

U.S. PATENT DOCUMENTS 2,781,407 A    2/1957    Schmerling
3,819,714 A    6/1974    Bluestone et al.
(Continued)

FOREIGN PATENT DOCUMENTS

CN    101116828 A    2/2008
CN    102050687 A    5/2011
(Continued)

OTHER PUBLICATIONS

Antoniotti et al., "Metal Triflimidates: Better than Metal Triflates as Catalysts in Organic Synthesis—The Effect of a Highly Delocalized Counteranion", Angewandte Chemie International Edition, vol. 49, No. 43, Oct. 18, 2010, pp. 7860-7888.
(Continued)

*Primary Examiner* — Sudhakar Katakam
*Assistant Examiner* — Jennifer C Sawyer
(74) *Attorney, Agent, or Firm* — Morrison & Foerster LLP

(57) ABSTRACT

The present disclosure provides methods to produce para-xylene, toluene, and other compounds from renewable sources (e.g., cellulose, hemicellulose) and ethylene in the presence of an acid, such as a Lewis acid. For example, cellulose and/or hemicellulose may be converted into 2,5-dimethylfuran (DMF) and 2-methylfuran, which may be converted into para-xylene and toluene, respectively. In
(Continued)

particular, para-xylene can then be oxidized to form terephthalic acid.

44 Claims, 3 Drawing Sheets

Related U.S. Application Data

(60) Provisional application No. 61/651,594, filed on May 25, 2012, provisional application No. 61/611,114, filed on Mar. 15, 2012, provisional application No. 61/606,824, filed on Mar. 5, 2012, provisional application No. 61/535,853, filed on Sep. 16, 2011.

(51) Int. Cl.
    *C07C 2/52* (2006.01)
    *C07C 15/08* (2006.01)

(52) U.S. Cl.
    CPC .......... *C07C 15/08* (2013.01); *C07C 2521/18* (2013.01); *C07C 2527/02* (2013.01); *C07C 2527/053* (2013.01); *C07C 2527/08* (2013.01); *C07C 2527/10* (2013.01); *C07C 2527/122* (2013.01); *C07C 2527/126* (2013.01); *C07C 2527/128* (2013.01); *C07C 2527/132* (2013.01); *C07C 2527/133* (2013.01); *C07C 2527/135* (2013.01); *C07C 2527/138* (2013.01); *C07C 2527/14* (2013.01); *C07C 2527/16* (2013.01); *C07C 2529/08* (2013.01); *C07C 2529/14* (2013.01); *C07C 2529/24* (2013.01); *C07C 2531/02* (2013.01); *C07C 2531/04* (2013.01); *C07C 2531/12* (2013.01)

(56) References Cited

U.S. PATENT DOCUMENTS

| | | |
|---|---|---|
| 3,947,521 A | 3/1976 | Lasco |
| 4,335,049 A | 6/1982 | Hamada et al. |
| 7,060,862 B2 | 6/2006 | Jong et al. |
| 7,385,081 B1 | 6/2008 | Gong |
| 7,608,727 B2 | 10/2009 | Ishii et al. |
| 7,790,431 B2 | 9/2010 | Frost |
| 8,314,267 B2 | 11/2012 | Brandvold |
| 8,889,938 B2 | 11/2014 | Masuno et al. |
| 8,933,281 B2 | 1/2015 | Cortright |
| 8,962,902 B2 | 2/2015 | Blommel et al. |
| 8,969,640 B2 | 3/2015 | Blommel et al. |
| 9,260,359 B2 | 2/2016 | Masuno et al. |
| 2010/0331568 A1 | 12/2010 | Brandvold |
| 2012/0029257 A1 | 2/2012 | Chen et al. |
| 2013/0245316 A1 | 9/2013 | Masuno et al. |
| 2014/0273118 A1 | 9/2014 | Held et al. |
| 2014/0275571 A1 | 9/2014 | Beck et al. |
| 2014/0296600 A1 | 10/2014 | Dauenhauer et al. |
| 2014/0349361 A1 | 11/2014 | Blommel et al. |
| 2014/0350294 A1 | 11/2014 | Masuno et al. |
| 2014/0350317 A1 | 11/2014 | Blommel et al. |
| 2015/0020797 A1 | 1/2015 | Eyal et al. |
| 2015/0028255 A1 | 1/2015 | Eyal et al. |
| 2015/0048274 A1 | 2/2015 | Eyal et al. |
| 2015/0141667 A1 | 5/2015 | Blank et al. |
| 2015/0141695 A1 | 5/2015 | Masuno et al. |
| 2015/0266793 A1 | 9/2015 | Masuno et al. |
| 2016/0368837 A1 | 12/2016 | Masuno et al. |

FOREIGN PATENT DOCUMENTS

| | | |
|---|---|---|
| CN | 102482177 A | 5/2012 |
| EP | 2061860 A1 | 5/2009 |
| FR | 2551071 A1 | 3/1985 |
| JP | 2000-136304 A | 5/2000 |
| JP | 2000-169425 A | 6/2000 |
| JP | 2003-104916 A | 4/2003 |
| JP | 2004-168831 A | 6/2004 |
| JP | 2004-244579 A | 9/2004 |
| JP | 2009-242251 A | 10/2009 |
| SU | 844617 A1 | 7/1981 |
| WO | 2008/109877 A1 | 9/2008 |
| WO | 2009/110402 A1 | 9/2009 |
| WO | 2010/148049 A2 | 12/2010 |
| WO | 2010/148081 A2 | 12/2010 |
| WO | 2010/151346 A1 | 12/2010 |
| WO | 2012/061272 A2 | 5/2012 |
| WO | 2012/092436 A1 | 7/2012 |
| WO | 2013/040514 A1 | 3/2013 |
| WO | 2014/043468 A1 | 3/2014 |
| WO | 2014/065657 A1 | 5/2014 |
| WO | 2014/152370 A2 | 9/2014 |
| WO | 2014/190124 A1 | 11/2014 |
| WO | 2014/190161 A1 | 11/2014 |

OTHER PUBLICATIONS

Baldwin et al., "Rearrangements of Toluene and Cycloheptatriene Cations", J. Am. Chem. Soc., vol. 97, No. 21, 1975, pp. 6169-6174.

Bautista et al., "Acetonylacetone Conversion on AIPO4-Cesium Oxide (5-30 wt%) Catalysts", Catalysis Letters, vol. 60, 1999, pp. 145-149.

Brasholz et al., "Highly Efficient Dehydration of Carbohydrates to 5-(chloromethyl)Furfural(CMF), 5-(hydroxymethyl)Furfural (HMF) and Levulinic Acid by Biphasic Continuous Flow Processing", Green Chemistry, vol. 13, 2011, pp. 1114-1117.

Chang et al., "Ultra-Selective Cycloaddition of Dimethylfuran for Renewable P-Xylene with H-BEA", Green Chemistry, The Royal Society of Chemistry, 2013, 4 pages.

Cheng et al., "Production of Targeted Aromatics by using Diels—Alder Classes of Reactions with Furans and Olefins over ZSM-5", Green Chemistry, vol. 14, Oct. 2012, pp. 3114-3125.

Cheng, Yu-Ting, "Catalytic Fast Pyrolysis of Furan Over ZSM-5 Catalysts: A Model Biomass Conversion Reaction", Sep. 2012, 165 pages.

Chidambaram et al., "A Two-Step Approach for the Catalytic Conversion of Glucose to 2,5-Dimethylfuran in Ionic Liquids", Green Chemistry, vol. 12, 2010, pp. 1253-1262.

Dauenhauer et al., "Renewable Catalytic Process for the Production of P-Xylene", Abstracts of Papers, 246th ACS National Meeting & Exposition, Indianapolis, Sep. 8-12, 2013, 1 page.

Deutsch et al., "Active Species of Copper Chromite Catalyst in C—O Hydrogenolysis of 5-Methylfurfuryl Alcohol", Journal of Catalysis, vol. 285, No. 1, Jan. 2012, pp. 235-241.

Do et al., "Elucidation of Diels-Alder Reaction Network of 2,5-Dimethylfuran and Ethylene on HY Zeolite Catalyst", ACS Catal., vol. 3, 2013, pp. 41-46.

Farina et al., "The Stille Reaction", Organic Reactions, vol. 50, 1997, 93 pages.

Fraile et al., "ZnCl2, ZnI2, and TiCl4 Supported on Silica Gel as Catalysts for the Diels-Alder Reactions of Furan", Journal of Molecular Catalysis A: Chemical, vol. 123, 1997, pp. 43-47.

Hanamoto et al., "Palladium-Catalyzed Carbonylative Coupling of Tributyl(1-Fluorovinyl)stannane with Aryl Halides and Aryl Triflates", Bulletin of the Chemical Society of Japan, vol. 75, No. 11, 2002, pp. 2497- 2502.

Hashimoto et al., "Measurement of Brønsted Acid and Lewis acid strength distributions of Solid Acid Catalysts using Chemisorption Isotherms of Hammett Indicators", Ind. Eng. Chem. Res., vol. 27, No. 10, 1988, pp. 1792-1797.

Hayashi et al., "The HfCl4-Mediated Diels-Alder Reaction of Furan", Angewandte Chemie International Edition, vol. 41, No. 21, 2002, pp. 4079-4082.

International Preliminary Report on Patentability received for PCT Patent Application No. PCT/US2012/055651 mailed on Mar. 27, 2014, 6 pages.

International Preliminary Report on Patentability received for PCT Patent Application No. PCT/US2013/59660 mailed on Mar. 26, 2015, 9 pages.

(56) References Cited

OTHER PUBLICATIONS

International Search Report and Written Opinion received for PCT Patent Application No. PCT/US2012/055651 mailed on Dec. 19, 2012, 8 pages.
International Search Report and Written Opinion received for PCT Patent Application No. PCT/US2013/059660 mailed on Nov. 25, 2013, 15 pages.
Jarzeücki et al., "Thermal Rearrangements of Norcaradiene", J. Am. Chem. Soc., vol. 121, No. 29, 1999, pp. 6928-6935.
Kandil et al., "The Synthesis and Characterization of New Schiff Bases and Investigating them in Solvent Extraction of Chromium and Copper", Separation Science and Technology, vol. 47, 2012, pp. 1754 1761.
Kobayashi et al., "Development of Novel Lewis Acid Catalysts for Selective Organic Reactions in Aqueous Media", Accounts of Chemical Research, vol. 35, No. 4, 2002, pp. 209-217.
Kobayashi et al., "Lewis Acid Catalysts Stable in Water. Correlation between Catalytic Activity in Water and Hydrolysis Constants and Exchange Rate Constants for Substitution of Inner-Sphere Water Ligands", J. Am. Chem. Soc., vol. 120, No. 32, 1998, pp. 8287-8288.
Kobayashi et al., "Rare-Earth Metal Triflates in Organic Synthesis", Chem. Rev. vol. 102, 2002, pp. 2227-2302.
Lessard et al., "High Yield Conversion of Residual Pentoses into Furfural via Zeolite Catalysis and Catalytic Hydrogenation of Furfural to 2-Methylfuran", Topics in Catalysis, vol. 53, No. 15-18, Sep. 2010, pp. 1231-1234.
Li et al., "Production and Separation of Phenols from Biomass-Derived Bio-Petroleum", Journal of Analytical and Applied Pyrolysis, vol. 89, 2010, pp. 218-224.
Lin et al., "Aromatics from Lignocellulosic Biomass: Economic Analysis of the Production of P-Xylene from 5-Hydroxymethylfurfural", AlChE Journal, vol. 59, No. 6, Jun. 2013, pp. 2079-2087.
McClure et al., "Diels-Alder Reactivity of a Ketovinylphosphonate with Cyclopentadiene and Furan", Tetrahedron Letters, vol. 37, No. 13, 1996, pp. 2149-2152.
Moore et al., "Catalyzed Addition of Furan with Acrylic Monomers", J. Org. Chem., vol. 48, No. 7, 1983, pp. 1105-1106.
Nikbin et al., "A DFT Study of the Acid-Catalyzed Conversion of 2,5-Dimethylfuran and Ethylene to p-xylene", Journal of Catalysis, vol. 297, 2013, pp. 35-43.
Non Final Office Action received for U.S. Appl. No. 13/838,761, mailed on Jan. 16, 2014, 6 pages.
Non-Final Office Action received for U.S. Appl. No. 14/519,034, mailed on Jul. 22, 2015, 9 pages.
Notice of Allowance received for U.S. Appl. No. 14/345,216, mailed on Oct. 6, 2015, 9 pages.
Notice of Allowance received for U.S. Appl. No. 13/838,761, mailed on Jul. 21, 2014, 9 pages.
Otto et al., "Catalysis of Diels-Alder Reactions in Water", Rijksuniversiteit Groningen, Aug. 3, 1971, 203 pages.
Otto et al., "Diels-Alder Reactions in Water", Pure Appl. Chem., vol. 72, No. 7, 2000, pp. 1365-1372.
Padwa et al., "Diels-Alder Reaction of 2-Amino-Substituted Furans as a Method for Preparing Substituted Anilines", J. Org. Chem., vol. 62, No. 12, 1997, pp. 4088-4096.
Papadogianakis et al., "Catalytic Conversions in Water: A Novel Carbonylation Reaction Catalysed by Palladium Trisulfonated Triphenylphosphine Complexes", J. Chem. Soc., Chem. Commun., 1994, pp. 2659-2660.
Prakash et al., "Gallium(III) Triflate: An Efficient and a Sustainable Lewis Acid Catalyst for Organic Synthetic Transformations", Acc. Chem. Res., vol. 45, No. 4, 2012, pp. 565-577.
Rebacz, Natalie A., "Hydration and Hydrolysis with Water Tolerant Lewis Acid Catalysis in High Temperature Water", A Dissertation Submitted in Partial Fulfillment of the Requirements for the Degree of Doctor of Philosophy (Chemical Engineering) in the University of Michigan, 2011, 164 pages.
Robbins et al., "A C—H Borylation Approach to Suzuki-Miyaura Coupling of Typically Unstable 2-Heteroaryl and Polyfluorophenyl Boronates", Organic Letters, vol. 14, No. 16, 2012, pp. 4266-4269.
Ruttink et al., "Complexation of Divalent Metal Ions with Diols in the Presence of Anion Auxiliary ligands: Zinc-Induced Oxidation of Ethylene Glycol to Glycolaldehyde by Consecutive Hydride Ion and Proton Shifts", J. Mass. Spectrom., vol. 47, 2012, pp. 869-874.
Rylander, Paul N., "Catalytic Hydrogenation over Platinum Metals", Academic Press Inc. 111 Fifth Avenue, New York, NY 10003, Jun. 1967, 565 pages.
Schwarz et al., "Methods for Preparation of Catalytic Materials", Chem. Rev., vol. 95, No. 3, 1995, pp. 477-510.
Shiramizu et al., "On the Diels-Alder Approach to Solely Biomass-Derived Polyethylene Terephthalate (PET): Conversion of 2,5-Dimethylfuran and Acrolein into p-xylene.", Chem. Eur. J., vol. 17, 2011, pp. 12452-12457.
Spillman et al., "Formation and Degradation of Furfuryl Alcohol, 5-Methylfurfuryl Alcohol, Vanillyl Alcohol, and Their Ethyl Ethers in Barrel-Aged Wines", J. Agric. Food Chem, vol. 46, No. 2, 1998, pp. 657-663.
Wahyudiono et al., "Supercritical Water as a Reaction Medium for Nitrogen-Containing Heterocycles", Journal of Chemistry and Chemical Engineering, vol. 6, 2012, pp. 897-910.
Wang et al., "Selective Production of Aromatics from Alkylfurans over Solid Acid Catalysts", ChemCatChem, vol. 5, 2013, pp. 2044-2050.
Williams et al., "Cycloaddition of Biomass-Derived Furans for Catalytic Production of Renewable P-Xylene", ACS Catal., vol. 2, 2012, pp. 935-939.
Wong et al., "Arene Syntheses by Dehydration of 7-Oxabicyclo[2.2.1]heptene Systems", Heterocycles, vol. 22, No. 4, 1984, pp. 875-890.
Xu et al., "A Novel Cis-Chelated Pd(II)—NHC Complex for Catalyzing Suzuki and Heck-Type Cross-Coupling Reactions", Tetrahedron, vol. 61, 2005, pp. 11225-11229.
Non-Final Office Action received for U.S. Appl. No. 15/003,613, mailed on Oct. 7, 2016, 11 pages.
Non-Final Office Action received for U.S. Appl. No. 14/428,339, mailed on Oct. 7, 2016, 14 pages.
Nie et al., "Copper (II) Bis((Trifluoromethyl) Sulfonyl) Amide. A Novel Lewis Acid Catalyst in Diels-Alder Reactions of Cyclopentadiene with Methyl Vinyl Ketone", Catalysis Today, vol. 36, 1997, pp. 81-84.
Reymond et al., "Copper-Catalyzed Diels-Alder Reactions", Chemical Reviews, vol. 108, 2008, pp. 5359-5406.

METHODS OF PRODUCING PARA-XYLENE AND TEREPHTHALIC ACID

CROSS-REFERENCE TO RELATED APPLICATIONS

This is a continuation application of U.S. application Ser. No. 14/345,216 filed Sep. 14, 2012 (Int'l), now issued as U.S. Pat. No. 9,260,359, which is a national phase patent application of PCT/US2012/055651, filed on Sep. 14, 2012, which claims priority to U.S. Provisional Patent Applications Nos. 61/535,853, filed Sep. 16, 2011, 61/606,824, filed Mar. 5, 2012, 61/611,114, filed Mar. 15, 2012, and 61/651,594, filed May 25, 2012, which are incorporated herein by reference in their entireties.

FIELD

The present disclosure relates generally to the production of para-xylene and terephthalic acid, and more specifically to the production of para-xylene and terephthalic acid from renewable biomass resources (e.g., cellulose, hemicellulose) and ethylene.

BACKGROUND

There exists a high demand to produce para-xylene and terephthalic acid from renewable biomass resources for use in the manufacture of clothing and plastics. Terephthalic acid is a precursor of polyethylene terephthalate (PET), which may be used to manufacture polyester fabrics. Terephthalic acid may be produced by oxidation of para-xylene. Commercial production of para-xylene is typically accomplished by catalytic reforming of petroleum derivatives; however, the use of petroleum-based feedstocks to commercially produce para-xylene (and hence terephthalic acid) generates greenhouse gas emissions and perpetuates reliance on petroleum resources. Alternative methods to produce para-xylene from renewable biomass resources have been under investigation. Biomass containing cellulose and/or hemicellulose can be converted into DMF. Then, DMF may be converted into para-xylene by cycloaddition of ethylene. Specifically, DMF and ethylene may be reacted in the presence of activated carbon to produce para-xylene; however, this reaction produce para-xylene in low yields, making these conditions commercially impracticable. Thus, what is needed in the art is a method to produce para-xylene and terephthalic acid in higher yields.

BRIEF SUMMARY

The present disclosure addresses this need by providing methods to produce para-xylene from 2,5-dimethylfuran (DMF) in higher yields than what is currently known in the art. The methods provided herein use Lewis acids to convert DMF into para-xylene. Without wishing to be bound by any theory, higher yields for producing para-xylene may be achieved by reducing the amount of 2,5-hexanedione formed from DMF or by converting any 2,5-hexanedione formed into para-xylene. The para-xylene produced can be oxidized to produce terephthalic acid.

One aspect of the disclosure provides a method A for producing a compound of formula I, wherein formula I has the structure:

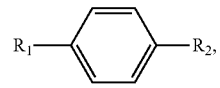
(formula I)

in which each $R_1$ and $R_2$ is independently an optionally substituted member chosen from alkyl, cycloalkyl, heterocycloalkyl, carboxyl, aryl, heteroaryl, hydrido, and arylalkyl; in which the method includes: a) providing a compound of formula II, wherein formula II has the structure:

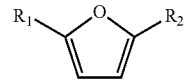
formula (II)

b) providing ethylene; and c) combining the compound of formula II and ethylene in the presence of an acid, a desiccant, or an acid and a desiccant to produce a reaction mixture that includes the compound of formula I, wherein less than 10% of the reaction mixture is a compound of formula III, wherein formula III has the structure,

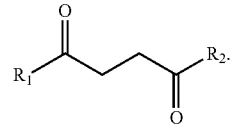
(formula III)

In some embodiments of method A, each $R_1$ and $R_2$ is independently an optionally substituted alkyl or carboxyl. In one embodiment, $R_1$ and $R_2$ is methyl. In another embodiment, $R_1$ and $R_2$ is carboxyl. In yet another embodiment, the compound of formula I is para-xylene, the compound of formula II is 2,5-dimethylfuran (DMF), and the compound of formula III is 2,5-hexanedione. In yet another embodiment, the compound of formula I is terephthalic acid, the compound of formula II is 2,5-furandicarboxylic acid (FDCA), and the compound of formula III is 2,5-dioxohexanedioic acid.

In some embodiments that may be combined with any of the preceding embodiments of method A, the method further includes producing one or more plastics or fuels from the compound of formula I.

In some embodiments that may be combined with any of the preceding embodiments of method A, the acid is a Lewis acid. In some embodiments of method A, the acid is a Lewis acid that reacts with water. In certain embodiments of method A, the acid is chosen from acetic acid, trichloroacetic acid, trifluoroacetic acid, phosphorus pentoxide, titanium chloride, boron trifluoride, boron trichloride, tin chloride, tin bromide, iron chloride, iron bromide, lanthanum triflate, aluminum triflate, and a combination thereof. In some embodiments that may be combined with any of the preceding embodiments of method A, the desiccant is a Lewis acid. In some embodiments, the desiccant is a Lewis acid that reacts with water. In some embodiments of method A, the desiccant is chosen from acetic anhydride, trichloroacetic anhydride, trifluoroacetic anhydride, hexafluoroacetic anhydride, aluminum trichloride, tin chloride, iron chloride, boron trifluoride, lanthanum trichloride, tantalum chloride, activated alumina, aerogel, bentonite clay, calcium chloride, calcium hydride, calcium sulfate, cobalt chloride, copper sulfate, lithium chloride, lithium hydride, lithium bromide, magnesium sulfate, magnesium perchlorate, molecular sieve, phosphorus pentachloride, phosphorus pentoxide, potassium carbonate, silica gel, sodium chlorate, sodium chloride, sodium sulfate, and sucrose. In certain embodiments, the desiccant is acetic anhydride, trichloroacetic anhydride, trifluoroacetic anhydride, phosphorus pentoxide, calcium chloride, a 4 Å molecular sieve, or silica gel. In one embodiment of method A, the acid acts as a desiccant.

In yet other embodiments that may be combined with the preceding embodiments of method A, the method further includes adding one or more molecular sieves to the reaction mixture. In some embodiments of method A, the one or more molecular sieves has a pore size of 3 Å to 100 Å. In another embodiment, the one or more molecular sieves has a pore size between 4 Å to 10 Å. In yet another embodiment, the one or more molecular sieves has a pore size of 3 Å to 5 Å. In one embodiment, the one or more molecular sieves has a pore size of 3 Å, 4 Å, or 5 Å. In yet other embodiments, the one or more molecular sieves are two molecular sieves, wherein the two molecular sieves independent have a pore size of 3 Å to 100 Å, 4 Å to 10 Å, or 3 Å to 5 Å. In one embodiment, the first molecular sieve has a pore size of 3 Å to 100 Å, and the second molecular sieve has a pore size of 3 Å to 5 Å.

In some embodiments that may be combined with the preceding embodiments of method A, the method further includes heating the reaction mixture to a temperature sufficient to form the compound of formula I. In some embodiments of method A, the reaction mixture is heated to a temperature between 0° C. and 400° C. In other embodiments that may be combined with the preceding embodiments of method A, the method is performed at a pressure sufficient to form the compound of formula I. In some embodiments of method A, the ethylene is provided at a pressure from about 20 barg to about 1000 barg. In other embodiments of method A, the method is performed at a supercritical temperature and a supercritical pressure. In one embodiment of method A, the method is performed at a temperature of about 147-152° C. (i.e., 420-425 K) and a pressure of about 40-60 barg.

In other embodiments that may be combined with the preceding embodiments of method A, wherein the compound of formula I is obtained from cellulose, hemicellulose, or a combination thereof Provided is also the use of the compound of formula I produced by method A for the manufacture of a plastic or fuel.

One aspect of the disclosure provides a method B for producing para-xylene by: a) providing 2,5-dimethylfuran (DMF); b) providing ethylene; and c) combining the DMF and the ethylene in the presence of an acid, a desiccant, or an acid and a desiccant to produce a reaction mixture comprising para-xylene, wherein less than 10% of the reaction mixture is 2,5-hexanedione. In some embodiments of method B, the method further includes oxidizing the para-xylene to produce terephthalic acid. In some embodiments that may be combined with the preceding embodiments of method B, the method further includes producing one or more plastics or fuels from the para-xylene.

In some embodiments that may be combined with any of the preceding embodiments of method B, the acid is a Lewis acid. In some embodiments of method B, the acid is a Lewis acid that reacts with water. In certain embodiments of method B, the acid is chosen from acetic acid, trichloroacetic acid, trifluoroacetic acid, phosphorus pentoxide, titanium chloride, boron trifluoride, boron trichloride, tin chloride, tin bromide, iron chloride, iron bromide, lanthanum triflate, aluminum triflate, and a combination thereof. In some embodiments that may be combined with any of the preceding embodiments of method B, the desiccant is a Lewis acid. In some embodiments, the desiccant is a Lewis acid that reacts with water. In some embodiments of method B, the desiccant is chosen from acetic anhydride, trichloroacetic anhydride, trifluoroacetic anhydride, hexafluoroacetic anhydride, aluminum trichloride, tin chloride, iron chloride, boron trifluoride, lanthanum trichloride, tantalum chloride, activated alumina, aerogel, bentonite clay, calcium chloride, calcium hydride, calcium sulfate, cobalt chloride, copper sulfate, lithium chloride, lithium hydride, lithium bromide, magnesium sulfate, magnesium perchlorate, molecular sieve, phosphorus pentachloride, phosphorus pentoxide, potassium carbonate, silica gel, sodium chlorate, sodium chloride, sodium sulfate, and sucrose. In certain embodiments, the desiccant is acetic anhydride, trichloroacetic anhydride, trifluoroacetic anhydride, phosphorus pentoxide, calcium chloride, a 4 Å molecular sieve, or silica gel. In one embodiment of method B, the acid acts as a desiccant.

In yet other embodiments that may be combined with the preceding embodiments of method B, the method further includes adding one or more molecular sieves to the reaction mixture. In some embodiments, the one or more molecular sieves has a pore size of 3 Å to 100 Å. In another embodiment, the one or more molecular sieves has a pore size between 4 Å to 10 Å. In yet another embodiment, the one or more molecular sieves has a pore size of 3 Å to 5 Å. In one embodiment, the one or more molecular sieves has a pore size of 3 Å, 4 Å, or 5 Å. In yet other embodiments, the one or more molecular sieves are two molecular sieves, wherein the two molecular sieves independent have a pore size of 3 Å to 100 Å, 4 Å to 10 Å, or 3 Å to 5 Å. In one embodiment, the first molecular sieve has a pore size of 3 Å to 100 Å, and the second molecular sieve has a pore size of 3 Å to 5 Å.

In some embodiments that may be combined with the preceding embodiments of method B, the method further includes heating the reaction mixture to a temperature sufficient to form the para-xylene. In some embodiments of method B, the reaction mixture is heated to a temperature between 0° C. and 400° C. In other embodiments that may be combined with the preceding embodiments of method B, the method is performed at a pressure sufficient to form the para-xylene. In some embodiments of method B, the ethylene is provided at a pressure from about 20 barg to about 1000 barg. In other embodiments of method B, the method is performed at a supercritical temperature and a supercritical pressure. In one embodiment of method B, the method is performed at a temperature of about 147-152° C. (i.e., 420-425 K) and a pressure of about 40-60 barg.

In other embodiments that may be combined with the preceding embodiments of method B, wherein the DMF is obtained from cellulose, hemicellulose, or a combination thereof Provided is also the use of the para-xylene produced by method B for the manufacture of a plastic or a fuel.

Another aspect of the disclosure provides a method C for producing terephthalic acid by: a) providing 2,5-furandicarboxylic acid (FDCA); b) providing ethylene; and c) combining the FDCA and ethylene in the presence of an acid, a desiccant, or an acid and a desiccant to produce a reaction mixture comprising terephthalic acid. In some embodiments of method C, less than 10% of the reaction mixture is one or more byproducts of FDCA. In some embodiments that may be combined with the preceding embodiments of method C, the method further includes producing one or more plastics or fuels from the terephthalic acid.

In some embodiments that may be combined with any of the preceding embodiments of method C, the acid is a Lewis acid. In some embodiments of method C, the acid is a Lewis acid that reacts with water. In certain embodiments, the acid is chosen from acetic acid, trichloroacetic acid, trifluoroacetic acid, phosphorus pentoxide, titanium chloride, boron trifluoride, boron trichloride, tin chloride, tin bromide, iron chloride, iron bromide, lanthanum triflate, aluminum triflate, and a combination thereof. In some embodiments that may be combined with any of the preceding embodiments of method C, the desiccant is a Lewis acid. In some embodiments, the desiccant is a Lewis acid that reacts with water. In some embodiments of method C, the desiccant is chosen from acetic anhydride, trichloroacetic anhydride, trifluoroacetic anhydride, hexafluoroacetic anhydride, aluminum trichloride, tin chloride, iron chloride, boron trifluoride, lanthanum trichloride, tantalum chloride, activated alumina, aerogel, bentonite clay, calcium chloride, calcium hydride, calcium sulfate, cobalt chloride, copper sulfate, lithium chloride, lithium hydride, lithium bromide, magnesium sulfate, magnesium perchlorate, molecular sieve, phosphorus pentachloride, phosphorus pentoxide, potassium carbonate, silica gel, sodium chlorate, sodium chloride, sodium sulfate, and sucrose. In certain embodiments, the desiccant is acetic anhydride, trichloroacetic anhydride, trifluoroacetic anhydride, phosphorus pentoxide, calcium chloride, a 4 Å molecular sieve, or silica gel. In one embodiment of method C, the acid acts as a desiccant.

In yet other embodiments that may be combined with the preceding embodiments of method C, the method further includes adding one or more molecular sieves to the reaction mixture. In some embodiments, the one or more molecular sieves has a pore size of 3 Å to 100 Å. In another embodiment, the one or more molecular sieves has a pore size between 4 Å to 10 Å. In yet another embodiment, the one or more molecular sieves has a pore size of 3 Å to 5 Å. In one embodiment, the one or more molecular sieves has a pore size of 3 Å, 4 Å, or 5 Å. In yet other embodiments, the one or more molecular sieves are two molecular sieves, wherein the two molecular sieves independent have a pore size of 3 Å to 100 Å, 4 Å to 10 Å, or 3 Å to 5 Å. In one embodiment, the first molecular sieve has a pore size of 3 Å to 100 Å, and the second molecular sieve has a pore size of 3 Å to 5 Å.

In some embodiments that may be combined with the preceding embodiments of method C, the method further includes heating the reaction mixture to a temperature sufficient to form the terephthalic acid. In some embodiments of method C, the reaction mixture is heated to a temperature between 0° C. and 400° C. In other embodiments that may be combined with the preceding embodiments of method C, the method is performed at a pressure sufficient to form the terephthalic acid. In some embodiments of method C, the ethylene is provided at a pressure from about 20 barg to about 1000 barg. In other embodiments of method C, the method is performed at a supercritical temperature and a supercritical pressure. In one embodiment of method C, the method is performed at a temperature of about 147-152° C. (i.e., 420-425 K) and a pressure of about 40-60 barg.

In other embodiments that may be combined with the preceding embodiments of method C, wherein the FDCA is obtained from cellulose, hemicellulose, or a combination thereof Provided is also the use of the terephthalic acid produced by method C for the manufacture of a plastic or fuel.

Yet another aspect of the disclosure provides a method D for producing terephthalic acid by: a) producing para-xylene according to the method described herein; and b) oxidizing the para-xylene to produce terephthalic acid. In some embodiments of method D, the method further includes producing one or more plastics or fuels from the terephthalic acid.

Provided is also the use of the terephthalic acid produced by method D for the manufacture of a plastic or fuel.

Yet another aspect of the disclosure provides a method E for producing para-xylene by reacting 2,5-dimethylfuran and ethylene, in a suitable solvent such that the concentration of the 2,5-dimethylfuran is from about 1 to about 75% by weight in the suitable solvent, with a catalyst selected from the group consisting of Lewis acids such as aluminum chloride, zinc chloride, indium chloride, divalent transition metal ions of copper, nickel or cobalt or mixtures thereof, triflates such as the triflate of indium, copper, gadolinium, yttrium, and trivalent metal ions from the lanthanide series of elements, H—Y zeolite, copper on mordenite, mordenites, activated carbon, and molecular sieves, at a temperature greater than 150° C., at a pressure greater than 100 psig, and with a desiccant.

In some embodiments of method E, the suitable solvent is tetrahydrofuran, dimethylsulfoxide, dioxane, $C_1$ to $C_{10}$ alcohol, $C_2$ to $C_6$ ketone, $C_2$ to $C_{10}$ ester, $C_2$ to $C_{10}$ ether, chlorinated solvent, ethyl acetate, ethyl lactate, triacetin, dibutylphthalate, $C_1$ to $C_{10}$ aliphatic hydrocarbon solvent, or $C_6$ to $C_{12}$ aromatic hydrocarbon solvent. In one embodiment of method E, the suitable solvent is dioxane. In some embodiments that may be combined with the preceding embodiments of method E, the concentration of the 2,5-dimethylfuran is from about 3 to about 50% by weight in the suitable solvent.

In some embodiments that may be combined with the preceding embodiments of method E, the catalyst is aluminum chloride, copper triflate, indium triflate or gadolinium triflate. In other embodiments that may be combined with the preceding embodiments of method E, the desiccant is calcium sulfate, magnesium sulfate, molecular sieves, metal chloride or anhydride.

In some embodiments that may be combined with the preceding embodiments of method E, the 2,5-dimethylfuran is recovered and recycled in the reaction. In other embodiments that may be combined with the preceding embodiments of method E, upon completion of the reaction, the reaction mixture is filtered. In yet other embodiments that may be combined with the preceding embodiments of method E, the para-xylene is isolated from the reaction mixture by distillation. In yet other embodiments that may be combined with the preceding embodiments of method E, the yield of para-xylene is greater than 75% by weight after isolation. In yet other embodiments that may be combined with the preceding embodiments of method E, the temperature is from about 150° C. to about 300° C.

Provided is also the use of the para-xylene produced by method E for the manufacture of a plastic or fuel.

Yet another aspect of the disclosure provides a method F for producing para-xylene by reacting 2,5-dimethylfuran and ethylene, in a suitable solvent such that the concentration of the 2,5-dimethylfuran is from about 1 to about 75% by weight in the suitable solvent, with a catalyst selected from Lewis acids such as aluminum chloride, zinc chloride, indium chloride, divalent transition metal ions of copper, nickel or cobalt or mixtures thereof, triflates such as the triflate of indium, copper, gadolinium or yttrium, trivalent metal ions from the lanthanide series of elements, H—Y zeolite, copper on mordenite, mordenites, activated carbon, and molecular sieves, at a temperature greater than 150° C., at a pressure greater than 100 psig, and with a desiccant.

In some embodiments of method F, the suitable solvent is tetrahydrofuran, dimethylsulfoxide, dioxane, $C_1$ to $C_{10}$ alcohol, $C_2$ to $C_6$ ketone, $C_2$ to $C_{10}$ ester, $C_2$ to $C_{10}$ ether, chlorinated solvent, ethyl acetate, ethyl lactate, triacetin, dibutylphthalate, $C_1$ to $C_{10}$ aliphatic hydrocarbon solvent, or $C_6$ to $C_{12}$ aromatic hydrocarbon solvent. In one embodiment of method F, the suitable solvent is dioxane. In some embodiments that may be combined with the preceding embodiments of method F, the concentration of the 2,5-dimethylfuran is from about 3 to about 50% by weight in the suitable solvent.

In some embodiments that may be combined with the preceding embodiments of method F, the catalyst is aluminum chloride, copper triflate, indium triflate or gadolinium triflate. In other embodiments that may be combined with the preceding embodiments of method F, the desiccant is calcium sulfate, magnesium sulfate, molecular sieves, metal chloride or anhydride.

In some embodiments that may be combined with the preceding embodiments of method F, the 2,5-dimethylfuran is recovered and recycled in the reaction. In other embodiments that may be combined with the preceding embodiments of method F, upon completion of the reaction, the reaction mixture is filtered. In yet other embodiments that may be combined with the preceding embodiments of method F, the para-xylene is isolated from the reaction mixture by distillation. In yet other embodiments that may be combined with the preceding embodiments of method F, the yield of para-xylene is greater than 75% by weight after isolation. In yet other embodiments that may be combined with the preceding embodiments of method F, the catalyst is recovered and recycled in the reaction. In yet other embodiments that may be combined with the preceding embodiments of method F, the temperature is from about 150° C. to about 300° C.

Provided is also the use of the para-xylene produced by method F for the manufacture of a plastic or fuel.

Yet another aspect of the disclosure provides a method G for producing para-xylene by: reacting 2,5-dimethylfuran and ethylene, in a suitable solvent such that the concentration of the 2,5-dimethylfuran is from about 1 to about 75% by weight in the suitable solvent, with a metal containing catalyst selected from the group consisting essentially of Lewis acids, at a temperature greater than about 150° C., at a pressure greater than about 100 psig, and wherein the yield of para-xylene is greater than about 75% by weight. The Lewis acids may include aluminum chloride, zinc chloride, indium chloride, divalent transition metal ions of copper, nickel or cobalt or mixtures thereof such as $CuCl_2$ or $CoCl_2$, triflates such as the triflate of indium, copper, gadolinium or yttrium, trivalent metal ions from the lanthanide series of elements or mixtures thereof, wherein the metal catalyst is used alone or supported, such as on silica, alumina, mordenite, carbon, or other known supports.

In some embodiments of method G, the suitable solvent is tetrahydrofuran, dimethylsulfoxide, dioxane, $C_1$ to $C_{10}$ alcohol, $C_2$ to $C_6$ ketone, $C_2$ to $C_{10}$ ester, $C_2$ to $C_{10}$ ether, chlorinated solvent, ethyl acetate, ethyl lactate, triacetin, dibutylphthalate, $C_1$ to $C_{10}$ aliphatic hydrocarbon solvent, or $C_6$ to $C_{12}$ aromatic hydrocarbon solvent. In one embodiment of method G, the suitable solvent is dioxane. In certain embodiments that may be combined with the preceding embodiments of method G, the concentration of the 2,5-dimethylfuran is from about 3 to about 50% by weight in the suitable solvent.

In other embodiments that may be combined with the preceding embodiments of method G, the catalyst is aluminum chloride, copper triflate, indium triflate or gadolinium triflate. In yet other embodiments that may be combined with the preceding embodiments of method G, a desiccant is present. In one embodiment, the desiccant is calcium sulfate, magnesium sulfate, molecular sieves, metal chloride or anhydride.

In some embodiments that may be combined with the preceding embodiments of method G, the 2,5-dimethylfuran is recovered and recycled in the reaction. In other embodiments that may be combined with the preceding embodiments of method G, upon completion of the reaction, the reaction mixture is filtered. In yet other embodiments that may be combined with the preceding embodiments of method G, the para-xylene is isolated from the reaction mixture by distillation. In yet other embodiments that may be combined with the preceding embodiments of method G, the catalyst is recovered and recycled in the reaction. In certain embodiments that may be combined with the preceding embodiments of method G, the temperature is from about 200° C. to about 400° C. In yet other embodiments that may be combined with the preceding embodiments of method G, the yield of para-xylene is greater than about 85% by weight as shown either after isolation or by NMR analysis prior to isolation.

Provided is also the use of the para-xylene by method G for the manufacture of a plastic or fuel.

Yet another aspect of the disclosure provides a method H for producing para-xylene by: a) providing 2,5-dimethylfuran (DMF); b) providing ethylene; c) providing a Lewis acid; d) providing a solvent; e) combining the DMF, the ethylene, the Lewis acid, and the solvent to form a reaction mixture; and f) producing para-xylene from at least a portion of the DMF in the reaction mixture. In some embodiments of method H, the method further includes isolating the para-xylene from the reaction mixture.

In some embodiments of method H, the solvent is an aprotic solvent. In one embodiment, the aprotic solvent has a dipole moment above 0.1. In certain embodiments of the method H, the solvent is an ether. In one embodiment of method H, the solvent is selected from the group consisting of dioxane, glyme, diglyme, triglyme, and tetrahydrofuran. In a particular embodiment, the solvent is 1,4-dioxane.

In some embodiments that may be combined with the preceding embodiments of method H, the Lewis acid has a metal cation. In certain embodiments of method H, the Lewis acid may have a Group 3 metal cation, a Group 9 metal cation, a Group 10 metal cation, a Group 11 metal cation, or a metal cation from the lanthanide series. In other embodiments of method H, the Lewis acid has a divalent metal cation or a trivalent metal cation. The divalent metal cation may, for example, be selected from $Zn^{2+}$, $Cu^{2+}$, $Ni^{2+}$, and $Co^{2+}$. The trivalent metal cation may, for example, be selected from $Al^{3+}$, $In^{3+}$, $Fe^{3+}$, $La^{3+}$, $Gd^{3+}$, and $Y^{3+}$. In other embodiments of method H, the Lewis acid is water-stable. In certain embodiments of method H, the Lewis acid is selected from $AlCl_3$, $Bi(OTf)_3$, $CuCl_2$, $Cu(OTf)_2$, $CoCl_2$, $CrCl_3$, $Fe(OTf)_2$, $Gd(OTf)_3$, $InCl_3$, $In(OTf)_3$, $NiCl_2$, $Ni(OTf)_2$, $MnCl_2$, $SnCl_2$, $TiCl_4$, $VCl_2$, $Y(OTf)_3$, acetic acid, chloroacetic acid, and $P_2O_5$. In one embodiment, the Lewis acid $CuCl_2$ or $Cu(OTf)_2$. In another embodiment, the Lewis acid is $Y(OTf)_3$.

In some embodiments that may be combined with the preceding embodiments of method H, less than 10% of the reaction mixture is 2,5-hexanedione. In other embodiments of method H, at least a portion of the DMF is converted to para-xylene at a temperature of at least 150° C. In one embodiment of method H, at least a portion of the DMF is converted to para-xylene at a temperature of between 150° C. and 300° C.

In other embodiments that may be combined with the preceding embodiments of method H, the method further includes adding one or more molecular sieves to the reaction mixture. In one embodiment, the one or more molecular sieves has a pore size of 3 Å to 100 Å.

In some embodiments, the method for producing para-xylene, includes: a) providing 2,5-dimethylfuran (DMF); b) providing ethylene; c) providing a water-stable Lewis acid; d) providing a solvent; e) combining the DMF, the ethylene, the water-stable Lewis acid, and the solvent to form a reaction mixture; and f) producing para-xylene from at least a portion of the DMF in the reaction mixture.

In other embodiments, the method for producing para-xylene, includes: a) providing 2,5-dimethylfuran (DMF); b) providing ethylene; c) providing a Lewis acid; d) providing a solvent, wherein the solvent is an ether; e) combining the DMF, the ethylene, the Lewis acid, and the solvent to form a reaction mixture; and f) producing para-xylene from at least a portion of the DMF in the reaction mixture.

Provided is also the use of the para-xylene produced by method H for the manufacture of a plastic or a fuel.

Yet another aspect of the disclosure provides a method I for producing para-xylene, by: a) providing 2,5-dimethylfuran (DMF); b) providing ethylene; c) providing a Lewis acid, wherein the Lewis acid is selected from the group consisting of acetic acid, $AlCl_3$, $CuCl_2$, $Cu(OTf)_2$, $GdCl_3$, $Gd(OTf)_3$, $InCl_3$, $In(OTf)_3$, $YCl_3$, and $Y(OTf)_3$; d) combining the DMF, the ethylene, and the Lewis acid to form a reaction mixture; and e) producing para-xylene from at least a portion of the DMF in the reaction mixture. In certain embodiments of method H, the Lewis acid is $CuCl_2$, $Cu(OTf)_2$, or $Y(OTf)_3$.

Provided is also the use of the para-xylene produced by method I for the manufacture of a plastic or a fuel.

Provided is also a method for producing terephthalic acid, by: a) producing para-xylene according to any of the methods described above; and b) oxidizing the para-xylene to produce terephthalic acid.

Yet another aspect of the disclosure provides a method J for producing a compound of formula I, wherein formula I has the structure:

(formula I)

wherein each $R_1$ and $R_2$ is independently hydrogen or alkyl, and wherein the method includes:

a) providing a compound of formula II, wherein formula II has the structure:

(formula II)

b) providing ethylene;
c) providing a Lewis acid;
d) combining the compound of formula II, the ethylene and the Lewis acid to form a reaction mixture; and
e) producing a compound of formula I from at least a portion of the compound of formula II in the reaction mixture.

In some embodiments of method J, the method further includes providing a solvent and combining the compound of formula II, the ethylene, the Lewis acid and the solvent to form a reaction mixture.

In some embodiment of method J, each $R_1$ and $R_2$ is independently hydrogen or a $C_{1-10}$ alkyl. In one embodiment, $R_1$ and $R_2$ are each methyl. In another embodiment of method J, $R_1$ is H and $R_2$ is methyl.

In some embodiments that may be combined with the preceding embodiments of method J, the solvent is an ether. In certain embodiments, the solvent is a $C_{1-10}$ ether. In other embodiments, the solvent may be selected from dioxane, tetrahydrofuran, triglyme, and sulfolane. In one embodiment of method J, the solvent is 14-dioxane.

In some embodiments that may be combined with the preceding embodiments of method J, the Lewis acid has a transition metal cation. In other embodiments of method J, the Lewis acid is water-stable. In certain embodiments of method J, the Lewis acid is selected from $AlCl_3$, $Bi(OTf)_3$, $CuCl_2$, $Cu(OTf)_2$, $CoCl_2$, $CrCl_3$, $Fe(OTf)_2$, $Gd(OTf)_3$, $InCl_3$, $In(OTf)_3$, $NiCl_2$, $Ni(OTf)_2$, $MnCl_2$, $SnCl_2$, $TiCl_4$, $VCl_2$, $Y(OTf)_3$, acetic acid, chloroacetic acid, and $P_2O_5$. In one embodiment of method J, the Lewis acid is $CuCl_2$ or $Cu(OTf)_2$. In another embodiment of method J, the Lewis acid is $Y(OTf)_3$.

In some embodiments that may be combined with the preceding embodiments of method J, at least a portion of the DMF is converted to para-xylene at a temperature of at least 150° C. In other embodiments that may be combined with the preceding embodiments of method J, the method further includes adding one or more molecular sieves to the reaction mixture.

In some embodiments that may be combined with the preceding embodiments of method J, less than 10% of the reaction mixture is a compound of formula III, wherein formula III has the structure,

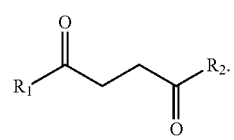
(formula III)

wherein $R_1$ and $R_2$ are the same as for formula I.

BRIEF DESCRIPTION OF THE DRAWINGS

The present application can be best understood by reference to the following description taken in conjunction with the accompanying drawing figures, in which like parts may be referred to by like numerals.

DETAILED DESCRIPTION

The following description sets forth numerous exemplary configurations, methods, parameters, and the like. It should be recognized, however, that such description is not intended as a limitation on the scope of the present disclosure, but is instead provided as a description of exemplary embodiments.

The following description relates to methods of producing commodity chemicals, such as para-xylene and terephthalic acid. For example, the methods described herein can produce para-xylene from 2,5-dimethylfuran (DMF) via a Diels-Alder reaction using ethylene as the dienophile. The ethylene used in the Diels-Alder reaction is unsubstituted. In some embodiments, para-xylene can be produced by: a) providing 2,5-dimethylfuran (DMF) and ethylene; b) combining the DMF and the ethylene in the presence of a Lewis acid and optionally a solvent to form a reaction mixture; and c) converting at least a portion of the DMF to para-xylene in the reaction mixture. Under certain conditions, the methods described herein may reduce the amount of byproducts formed from side reactions (e.g., decomposition of starting materials) and improve the yield of para-xylene produced from DMF.

Figure 1:
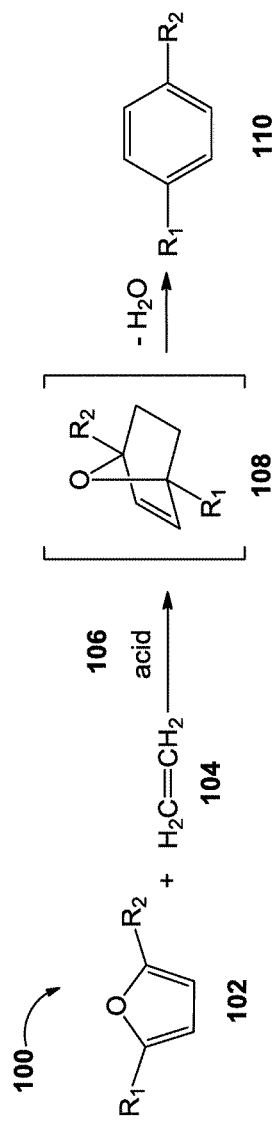
FIG. 1 depicts an exemplary reaction to produce a compound of formula I by cycloaddition of ethylene to a compound of formula II.

With reference to FIG. 1, reaction 100 is an exemplary embodiment for producing a compound of formula I (compound 110), which has the structure:

(formula I)

in which each $R_1$ and $R_2$ is independently hydrogen or alkyl. $R_1$ and $R_2$ may be the same or different substituents. For example, in one embodiment, $R_1$ and $R_2$ are both methyl. In another embodiment, $R_1$ is methyl, whereas $R_2$ is hydrogen. In yet another embodiment, $R_1$ is methyl, whereas $R_2$ is ethyl. In certain embodiments, at least one of $R_1$ and $R_2$ is other than hydrogen.

As used herein, "alkyl" encompasses straight chain and branched chain. Examples include methyl, ethyl, propyl, isopropyl, and butyl. The total number of carbon atoms in each such group is sometimes described herein, e.g., when the group can contain up to ten carbon atoms it can be represented as 1-10C or as C1-C10, C1-10 or $C_{1\text{-}10}$.

For example, when $R_1$ and $R_2$ are both methyl, the compound of formula I is para-xylene (or "p-xylene" or "PX"), which has the structure:

When $R_1$ is methyl and $R_2$ is hydrogen, the compound of formula I is toluene, which has the structure:

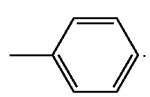

With reference again to FIG. 1, the method described herein employs various components, including a compound of formula II (compound 102), ethylene 104, an acid 106 and/or a desiccant, and optionally one or more solid catalysts (e.g., molecular sieves).

The compound of formula II has the structure:

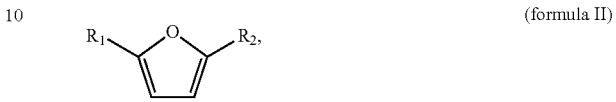
(formula II)

in which $R^1$ and $R^2$ are the same as in the compound of formula I.

When $R_1$ and $R_2$ are both methyl, the compound of formula II is 2,5-dimethylfuran (DMF), which has the structure:

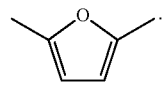

When $R_1$ is methyl and $R_2$ is hydrogen, the compound of formula II is 2-methylfuran, which has the structure:

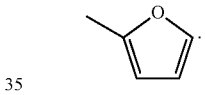

Figure 3:
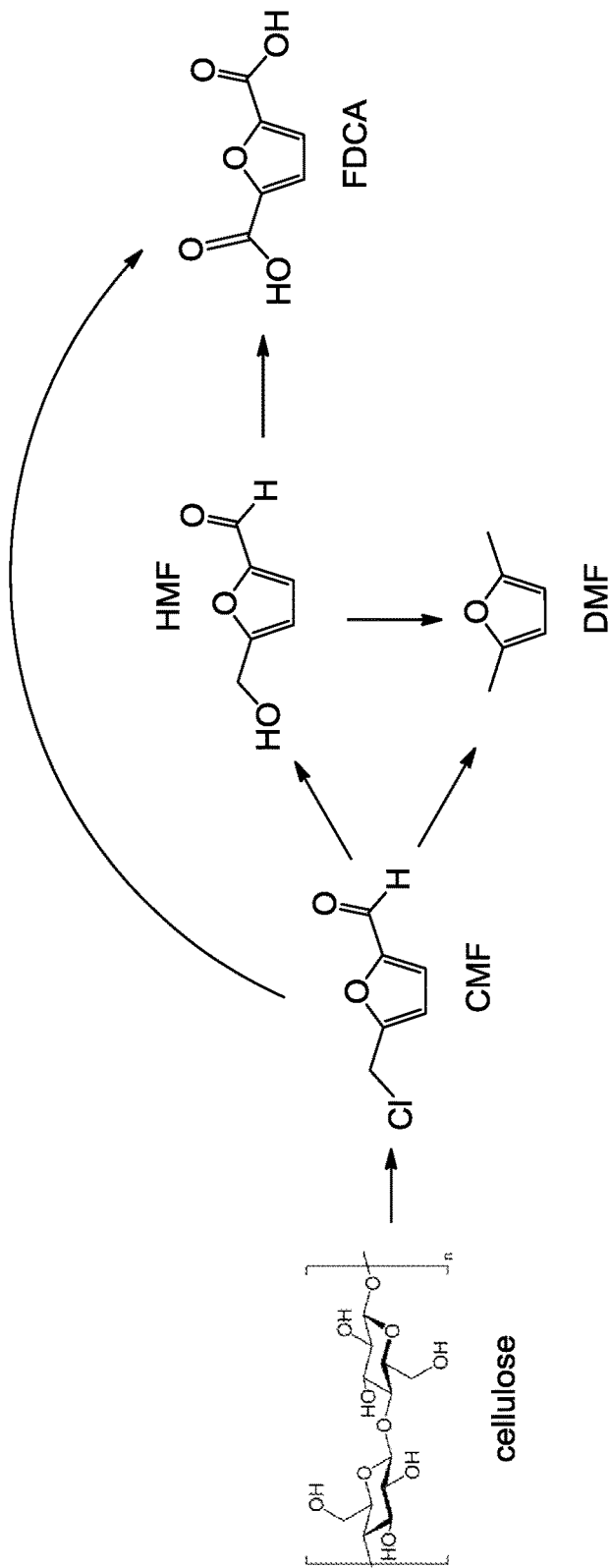
FIG. 3 depicts exemplary reaction pathways to produce DMF and FDCA from cellulosic materials.

When the compound of formula I is para-xylene, the compound of formula II is 2,5-dimethylfuran (DMF). When the compound of formula I is toluene, the compound of formula II is 2-methylfuran. The compound of formula I may be obtained from carbonaceous materials. One of skill in the art would know suitable methods to obtain DMF and 2-methylfuran from biomass. For example, with reference to FIG. 3, cellulose (and hemicellulose, if present) or other $C_6$ sugars (e.g., glucose, fructose) may be converted into halomethylfurfurals, such as 5-chloromethylfurfural (CMF), which may be converted into DMF either directly or via 5-hydroxymethylfurfural (HMF). It is also well known in the art that 2-methylfuran can be obtained from hemicellulose or other $C_5$ sugars (e.g., xylose), which can be converted to furfural and then reduced to 2-methylfuran. Examples of suitable carbonaceous materials from which the compound of formula I, such as DMF and 2-methylfuran, can be derived include agricultural materials (e.g., corn stover, rice hulls, peanut hulls, spent grains), processing waste (e.g., paper sludge), recycled cellulosic materials (e.g., cardboard, old corrugated containers (OCC), mixed paper, old newspaper (ONP)), as well as fructose (e.g., high fructose corn syrup), sucrose or glucose.

Figure 2:
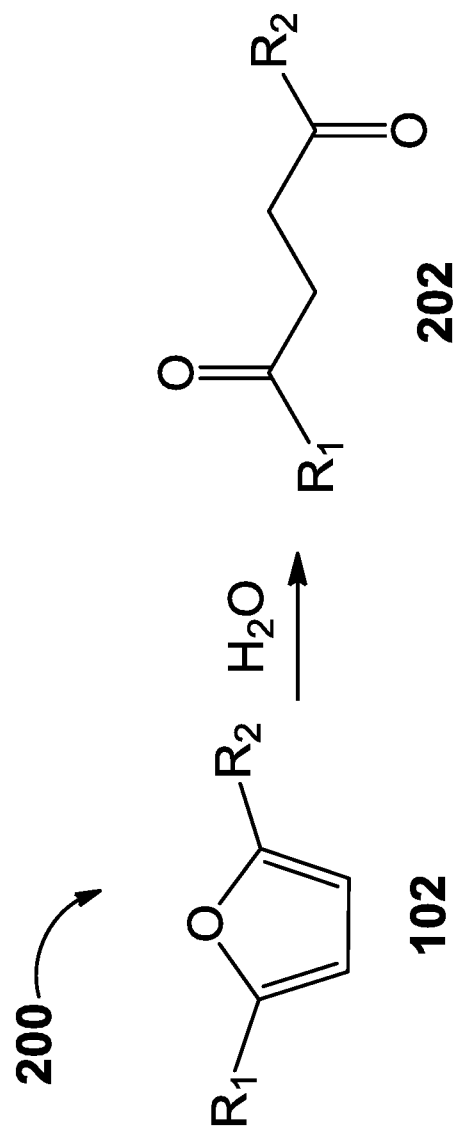
FIG. 2 depicts an exemplary side reaction, in which a compound of formula I decomposes in the presence of water to form a compound of formula III.

With reference to FIG. 2, certain embodiments are directed to the production of para-xylene by reacting DMF with ethylene under cycloaddition reaction conditions in the presence of an acid, a desiccant, or an acid and a desiccant to reduce the formation of a compound of formula III (compound 202), which has the structure:

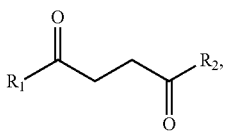

(formula III)

in which $R^1$ and $R^2$ are the same as in the compound of formula I.

In one embodiment, when the compound of formula I is para-xylene, the compound of formula III is 2,5-hexanedione:

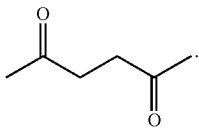

In another embodiment, when the compound of formula I is toluene, the compound of formula III is 4-oxopentanal:

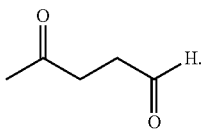

The methods described herein to convert a compound of formula II into a compound of formula I employ various catalysts, solvents, desiccants, and reaction conditions, each of which are described in further detail below.

Acid

With reference again to FIG. 1, in an exemplary embodiment, acid 106 is a Lewis acid. Without wishing to be bound by any theory, the acid may be catalyzing the ring opening and subsequent dehydration of the Diels-Alder cycloaddition adduct (intermediate 108).

In some embodiments, the Lewis acid may have a metal cation. In certain embodiments, the metal cation is a transition metal cation. For example, the metal cation may be selected from Group 3, Group 9, Group 10, Group 11, or the lanthanide series. In certain embodiments, the metal cation may be selected from Group 3, Group 9, Group 11, or the lanthanide series. It should be understood that the group number used for these metals follow the IUPAC or long-form nomenclature, which is well-known to one of ordinary skill in the art.

In other embodiments, the Lewis acid may have a divalent metal cation or a trivalent metal cation. For example, in certain embodiments, the divalent metal cation may be selected from $Zn^{2+}$, $Cu^{2+}$, $Ni^{2+}$, and $Co^{2+}$. In one embodiment, the divalent metal cation may be selected from $Zn^{2+}$, $Cu^{2+}$, and $Co^{2+}$. In certain embodiments, the trivalent metal cation may be selected from $Al^{3+}$, $In^{3+}$, $Fe^{3+}$, $La^{3+}$, $Gd^{3+}$, and $Y^{3+}$. In one embodiment, the trivalent metal cation may be selected from $Al^{3+}$, $In^{3+}$, $La^{3+}$, $Gd^{3+}$, and $Y^{3\pm}$. The divalent or trivalent metal cation of the Lewis acid may coordinate two or three counterions, respectively. The counterions may include, for example, halides, triflates (-OTf), or any combination thereof.

In some embodiments, the Lewis acid is selected from aluminum chloride, bismuth triflate, copper chloride, copper triflate, cobalt chloride, chromium chloride, iron triflate, gadolinium triflate, indium chloride, indium triflate, nickel chloride, manganese chloride, tin chloride, titanium chloride, vanadium chloride, yttrium triflate, zinc chloride, acetic acid, chloroacetic acid, dichloroacetic acid, trichloroacetic acid, fluoroacetic acid, difluoroacetic acid, trifluoroacetic acid, and phosphorus pentoxide. In certain embodiments, the Lewis acid is selected from aluminum chloride, copper triflate, copper chloride, and yttrium triflate. In one embodiment, the Lewis acid is copper triflate or copper chloride. In other embodiments, the Lewis acid is acetic acid, chloroacetic acid, or phosphorus pentoxide.

In some embodiments, the Lewis acid is selected from $AlCl_3$, acetic acid, chloroacetic acid, $BiCl_3$, $Bi(OTf)_3$, $CuCl_2$, $Cu(OTf)_2$, Cu(II) on mordenite, $CuCl_2$/alumina, $CuCl_2$/HY zeolite, $CoCl_2$, $CO(OTf)_2$, $CrCl_3$, $Cr(OTf)_3$, $FeCl_2$, $Fe(OTf)_2$, $CdCl_2$, $Cd(OTf)_2$, H—Y-Zeolite, $InCl_3$, $In(OTf)_3$, $NiCl_2$, $Ni(OTf)_2$, $MnCl_2$, $Mn(OTf)_2$, $P_2O_5$, $SnCl_2$, $Sn(OTf)_2$, $TiCl_4$, $Ti(OTf)_4$, $VCl_2$, $V(OTf)_2$, $YCl_3$, $Y(OTf)_3$, $ZnCl_2$, $Zn(OTf)_2$, $GdCl_3$, $Gd(OTf)_3$, $VCl_5$, $V(OTf)_5$. In certain embodiments, the Lewis acid is selected from $AlCl_3$, $Cu(OTf)_2$, $CuCl_2$, and $Y(OTf)_3$. In one embodiment, the Lewis acid is $Cu(OTf)_2$ or $CuCl_2$.

In some embodiments, the Lewis acid may be used alone or supported, for example, on silica, alumina, mordenite, carbon, zeolites, or other suitable supports known in the art. In certain embodiments, the Lewis acid is Cu (II) on mordenite, $CuCl_2$/alumina, or $CuCl_2$/HY zeolite. Solid supported acid catalysts can more easily be recovered, recycled, and used in a continuous process.

In other embodiments, the Lewis acid is selected from acetic acid, trichloroacetic acid, trifluoroacetic acid, phosphorus pentoxide, titanium chloride (e.g., $TiCl_4$), boron trifluoride ($BF_3$), boron trichloride ($BCl_3$), tin chloride (e.g., $SnCl_2$), tin bromide (e.g., $SnBr_2$), iron chloride (e.g., $FeCl_2$), iron bromide (e.g., $FeBr_2$), and various triflate metals (e.g., lanthanum triflate, and aluminum triflate).

In yet other embodiments, the Lewis acid is a water-stable Lewis acid. As used herein, "a water-stable Lewis acid" refers to a Lewis acid that is not deactivated by the presence of water in a given reaction. It should be understood, however, that a particular Lewis acid may show water stability for the purposes of one reaction, but not toward another. Water-stable acid catalysts can improve recyclability of the catalyst used in the reaction on industrial scale, since water can often be produced as a by-product in the reaction. In some embodiments, the water-stable Lewis acid may have a $pK_h$ between 4.3 and 10.08. $K_h$ is the hydrolysis constant. $pK_h$ is defined as follows:

$$pK_h = -\log K_{xy},$$

where $$K_{xy} = \frac{[M_x(OH)_y^{(xz-y)+}][H^+]^y}{[M^{z+}]^x} + \frac{g_{xy}g_{H^+}^y}{g_{M^{z+}}^y a_{H_2O}^y},$$

based on the following reaction: $x\ M^{2+} + y\ H_2O \rightleftharpoons M_x(OH)_y^{(xx-y)+} + y\ H^+$, where M is the metal cation. In other embodiments, the water-stable Lewis acid may have a water exchange rate constant of at least $3.2 \times 10^6\ M^{-1}s^{-1}$. See generally Kobayashi et al., J. Am. Chem. Soc. 1998, 120, 8287-8288.

Examples of water-stable Lewis acids may include those with a metal cation selected from Sc(III), Y(III), Ln(III), Fe(II), Cu(II), Zn(II), Cd(II), Pb(II), La(III), Ce(III), Pr(III), Nd(III), Sm(III), Eu(III), Gd(III), Tb(III), Dy(III), Ho(III), Er(III), Tm(III), Yb(III), and Lu(III). In certain embodiments, the Lewis acid may include Fe(II), Cu(II), Zn(II), Cd(II), Pb(II) Sc(III), Y(III), Ln(III), Mn(II), or Ag(I). Water-stable Lewis acids may include, for example, $ScCl_3$, $Sc(ClO_4)_3$, $Mn(ClO_4)_2$, $FeCl_2$, $Fe(ClO_4)_2$, $FeCl_3$, $Fe(ClO_4)_3$, $Co(ClO_4)_2$, $Ni(ClO_4)_2$, $CuCl_2$, $Cu(ClO_4)_2$, $ZnCl_2$, $Zn(ClO_4)_2$, $YCl_3$, $Y(ClO_4)_3$, $AgClO_4$, $CdCl_2$, $Cd(ClO_4)_2$, $InCl_3$, $In(ClO_4)_3$, $SnCl_2$, $La(OTf)_3$, $Ce(OTf)_3$, $Pr(OTf)_3$, $Nd(OTf)_3$, $Sm(OTf)_3$, $Eu(OTf)_3$, $Gd(OTf)_3$, $Tb(OTf)_3$, $Dy(OTf)_3$, $Ho(OTf)_3$, $Er(OTf)_3$, $Tm(OTf)_3$, $YbCl_3$, $Yb(ClO_4)_3$, $Yb(OTf)_3$, $Lu(OTf)_3$, $PbCl_2$, and $Pb(ClO_4)_2$.

In certain embodiments, the Lewis acid used in the reaction may be obtained from an anhydride that hydrolyzes into its corresponding acid form in the presence of water. For example, in one embodiment, acetic anhydride may be combined with DMF and ethylene, in which the acetic anhydride may contain a small percentage of acetic acid, which acts as a Lewis acid that catalyzes the reaction. Additionally, the acetic anhydride in the reaction mixture may further convert into acetic acid during the course of the reaction.

In other embodiments, the acids may also act as a desiccant ("acid desiccants"), and remove at least a portion of the water present in the reaction mixture. In certain embodiments, the acid desiccant may be a Lewis acid that is reactive with water. In one embodiment, the acid desiccant may be phosphorus pentoxide ($P_2O_5$). Other suitable acid desiccants may include, for example, aluminum trichloride, tin chloride, iron chloride, and boron trifluoride. A combination of acids may be used, as well as a combination of acids, acid desiccants and desiccants (described in further detail below) may be used.

It should be understood that a combination of acids described herein may also be used. The amount of acid used in the reaction may also vary depending on the type and amount of starting material, the type and amount of solvent (if present), and the reaction conditions used. In some embodiments, the acid is used in a catalytic amount. For example with respect to the reaction to convert DMF into para-xylene, in some embodiments, the acid is present at a concentration of between 0.5 wt % and 10 wt %, or between 0.5 wt % and 5 wt % of DMF.

Molecular Sieves

Furthermore, a solid catalyst such as a molecular sieve may optionally be added to the reaction mixture. Suitable molecular sieves may include, for example, aluminosilicate minerals, clays, porous glasses, microporous charcoals, zeolites, and activated carbons. Without wishing to be bound by theory, it is believed that the addition of a molecular sieve with a pore size of 4 Å to 10 Å will both catalyze the Diels-Alder reaction, as well as selectively remove water. In certain embodiments, the solid catalyst added to the reaction mixture has a pore size of 3 Å to 100 Å. Solid catalysts with pore sizes of 3 Å to 100 Å may be useful to catalyze the Diels-Alder reaction. In other embodiments, the solid catalyst added to the reaction mixture has a pore size of 3 Å to 5 Å, or 3 Å to 4 Å. Solid catalysts with pore sizes of 3 Å to 5 Å may be useful to remove water from the reaction. It should also be understood that two or more solid catalysts with different pore sizes may be used. For example, in some embodiments, a first solid catalyst and a second solid catalyst may be used, in which the first solid catalyst has a pore size between 3 Å to 100 Å, and the second solid catalyst has a pore size between 3 Å to 5 Å.

Solvent

A solvent may also be optionally added to the reaction mixture. In some embodiments, a solvent is added to the reaction mixture. A combination of solvents may also be used. The solvent can help dissolve and dilute the DMF, and lessen the bimolecular reaction of DMF with itself to form a polymer, which can be a side reaction that lowers the yield of para-xylene.

The solvent used typically has good solubility for ethylene and DMF, which can help to enhance the solvation effect and improve the reaction rate. Additionally, the solvent used is typically stable to the process conditions, and preferably can be recycled for use again in the reaction. The recyclability of the solvent is particularly useful for performing the methods described herein on a commercial scale.

Certain solvents may lead to high product yields under certain reaction conditions. For example, in some embodiments, the solvent is an aprotic solvent. In particular embodiments, the aprotic solvent may have a dipole moment above 0.1. One of skill in the art would understand that the dipole moment is a measure of polarity of a solvent. The dipole moment of a liquid can be measured with a dipole meter. Suitable aprotic solvents may include, for example, dimethylsulfoxide (DMSO), dimethylformamide (DMF), dimethylacetamide, dioxane, polyethers (including, for example, glyme, diglyme, triglyme, etc.), acetonitrile, sulfolane, ethers (including, for example, tetrahydrofuran, diethylether, dialkylether), nitromethane, anisole, nitrobenzene, and bromobenzene.

In certain embodiments, the solvent is an ether. For example, the solvent can be a $C_2$ to $C_{10}$ ether, which refers to an ether having 2 to 10 carbon atoms. It should be understood, however, that the ether can be an alkyl ether or a cycloalkyl ether. An alkyl ether may include, for example, diethyl ether, glycol dimethyl ether (glyme), diethylene glycol dimethyl ether (diglyme), or triethylene glycol dimethyl ether (triglyme). A cycloalkyl ether may include, for example, dioxane (e.g., 1,4-dioxane) and tetrahydrofuran. The ether may, in certain embodiments, be a polyether with two or more oxygen atoms. Suitable polyethers may include, for example, glyme, diglyme, triglyme, or tetraglyme.

In other embodiments, the ether solvent may have additional functional groups, such as alcohols. In one embodiment, the solvent is polyethylene glycol.

In particular embodiments, the solvent may be selected from dioxane, THF, DMSO, $C_1$ to $C_{10}$ alcohols, diglyme, $C_2$ to $C_{10}$ ethers, $C_2$ to $C_6$ ketones, chlorinated solvents, $C_2$ to $C_{10}$ esters, triacetin, dibutylphthalate, $C_1$ to $C_{10}$ aliphatic solvents, and $C_6$ to $C_{12}$ aromatic solvents, and mixtures thereof. $C_1$ to $C_{10}$ alcohols may include, for example, ethanol and propanol. $C_2$ to $C_{10}$ ethers may include, for example, dioxane, diethyl ether, triethylene glycol dimethyl ether (triglyme), and other glycol ethers. Chlorinated solvents may include, for example, carbon tetrachloride, chloroform and methylene chloride. $C_2$ to $C_{10}$ esters may include, for example, ethyl acetate, and ethyl lactate. $C_1$ to $C_{10}$ aliphatic solvents may include, for example, hexane and cyclohexane. $C_6$ to $C_{12}$ aromatic solvents may include, for example, toluene and octane.

In certain embodiments, the solvent is selected from dioxane, tetrahydrofuran, sulfolane, and triglyme. In one preferred embodiment, the solvent is 1,4-dioxane. The use of 1,4-dioxane may help with minimizing the self-condensation of DMF. Additionally, DMF and ethylene are soluble in dioxane at room temperature and ambient pressure based on NMR observations of the reaction products. Also dioxane is stable under the reaction conditions specified herein, such that no solvent by-products were observed by NMR. Any of the above indicated solvents which have these same properties as dioxane are suitable and considered to be suitable solvents.

The amount of solvent used may vary. For example, in some embodiments, the concentration of the DMF in the reaction mixture is from about 1 to about 75% by weight in the solvent, preferably from about 3 to about 50% by weight in the solvent.

Desiccant

In some embodiments, the method described herein may optionally include the addition of a desiccant. As discussed above, some of the Lewis acids may be an acid desiccant. In other embodiments, the desiccant described herein may not be a Lewis acid. A combination of desiccants may be used, including a combination of desiccants and acid desiccants.

In some embodiments, suitable desiccants that may be added to the reaction mixture include, for example, acetic anhydride, trichloroacetic anhydride, trifluoroacetic anhydride, hexafluoroacetic anhydride, aluminum trichloride, tin chloride, iron chloride, boron trifluoride, activated alumina, aerogel, bentonite clay, calcium chloride, calcium hydride, calcium sulfate, cobalt chloride, copper sulfate, lithium chloride, lithium hydride, lithium bromide, magnesium sulfate, magnesium perchlorate, molecular sieve, phosphorus pentachloride, phosphorus pentoxide, potassium carbonate, silica gel, sodium chlorate, sodium chloride, sodium sulfate, and sucrose. In certain embodiments, the desiccant is acetic anhydride, trichloroacetic anhydride, trifluoroacetic anhydride, phosphorus pentoxide, calcium chloride, a 4 Å molecular sieve, or silica gel.

In other embodiments, the desiccant may be selected from calcium sulfate, magnesium sulfate, molecular sieves, metal chlorides and anhydrides. Metal chlorides may include, for example, calcium chloride, barium chloride, or zinc chloride. Anhydrides may include, for example, acetic anhydride, chloroacetic anhydride, or the anhydride of phosphoric acid ($P_2O_5$). One skilled in the art would recognize that the anhydride may contain a small percentage of hydrolyzed anhydride, which is an acid. For example, less than 1% acetic acid may be present in acetic anhydride that is commercially purchased. Additionally, when anhydrides are used in the methods described herein, the presence of water in the reaction may cause the anhydride to convert into its hydrolyzed form, which is a Lewis acid.

Reaction Conditions

The reaction of the compound of formula II with ethylene proceeds in the presence of an acid, and optionally a desiccant and/or a solid catalyst, under suitable cycloaddition reaction conditions. The reaction temperature and/or pressure may affect the rate of the reaction, including the amount of the compound of formula I produced in the reaction, as well as the amount of byproducts produced (e.g., 2,5-hexanedione).

In some embodiments, the reaction proceeds at a temperature between 0° C. and 400° C., and a pressure between 10 barg to 1000 barg. In certain embodiments, the reaction temperature is between room temperature (e.g., 18° C.-22° C.) and 300° C.

In certain embodiments, the reaction temperature is at least 150° C., or at least 200° C. In other embodiments, the reaction temperature is between 100° C. and 300° C., between 150° C. and 400° C., between 150° C. and 300° C., between 125° C. and 175° C., between 200° C. to 350° C., between 200° C. to 250° C., between 200° C. and 400° C., between 220° C. to 230° C., or between 150° C. and 220° C. Higher temperatures can be used so long as the suitable solvent is stable.

In certain embodiments, the reaction pressure is between 20 barg to 1000 barg, between 50 barg to 1000 barg, between 100 barg to 1000 barg, between 150 barg to 500 barg, or between 35 and 38 barg.

In other embodiments, the reaction pressure may reflect the pressure at which ethylene is added to the reactor. The ethylene may be added at a pressure such that the concentration of this reactant is sufficiently high in the solvent for optimal reaction rates. In some embodiments, the ethylene pressure is at least 10 psig, 50 psig, or 100 psig.

It should be understood and clearly conveyed herein that the reaction temperature and reaction pressure may be the same as if each and every combination were individually listed. For example, in one variation, the method is carried out at a temperature of about 225° C. and a pressure of about 34 barg (equivalent to about 500 psig).

The method may also be carried out under supercritical conditions (e.g., supercritical pressures and/or supercritical temperatures). For example, in one embodiment, supercritical conditions may be used if a solvent is not used in the reaction. In one embodiment, the method is carried out at or above 49.7 barg and/or at or above 9° C. (i.e., 282 K). It should be understood that temperature may be expressed as degrees Celcius or degrees Kelvin. One of ordinary skill in the art would be able to convert the temperature described herein from one unit to another. Pressure may also be expressed as gauge pressure (barg), which refers to the pressure in bars above ambient or atmospheric pressure. Pressure may also be expressed as bar, atmosphere (atm), pascal (Pa) or pound-force per square inch (psi). One of ordinary skill in the art would be able to convert the pressure described herein from one unit to another.

The method may be carried out batch-wise or continuously. The time of the reaction will also vary with the reaction conditions and desired yield, but is generally about 1 to 72 hours. In some of the foregoing embodiments, the reaction time is determined by the rate of conversion of the starting material. In some of the foregoing embodiments, the reaction mixture is heated for 1 to 24 hours. In some of the foregoing embodiments, the reaction mixture is heated for 1 to 10 hours. In some of the foregoing embodiments, the reaction mixture is heated for 1 to 5 hours. In some of the foregoing embodiments, the reaction mixture is heated for 1 to 3 hours. In some of the foregoing embodiments, the reaction mixture is heated for less than 2 hours.

Isolation and Purification

The methods described herein may further include isolating the compound of formula I from the reaction mixture. Any methods known in the art may be employed to isolate the product. For example, the products may be isolated by distillation.

In one exemplary embodiment, to isolate para-xylene from the reaction mixture, the reaction mixture can be first filtered to remove any catalyst and desiccants (if present). The filtered mixture may then be transferred to a distillation column One of skill in the art would know how to recovery para-xylene by distillation since the boiling points of the various components of the reaction mixture are known, including the boiling points of the solvents used (e.g., 1,4-dioxane has a boiling point of 101° C.), para-xylene has a boiling point of 138° C., 2,5-hexanedione has a boiling point of 191° C., and DMF has a boiling point of 94° C. The solvent and DMF recovered can be recycled. The catalysts can be covered and recycled. Byproducts such as 2,5-hexanedione can also be recovered.

The methods described herein may also include purifying the isolated compound of formula I. Any suitable methods known in the art may be employed to purify the isolated compound, including for example column chromatography or recrystallization.

Yield, Conversion and Selectivity

The yield of a product takes into account the conversion of the starting materials into the product, and the selectivity for the product over other byproducts that may be formed.

The difference between yield, conversion and selectivity is explained in the example provided below. The exemplary reaction for converting DMF into para-xylene can be generalized as follows, where "A" represents the moles of DMF; "B" represents the mole of ethylene; "C" represents the mole of para-xylene; and "a", "b", "c" are stoichiometric coefficients.

$$aA + bB \rightarrow cC,$$

Conversion is the percentage of reactant A that has been consumed during the reaction shown above, as expressed by the following equation:

$$\% \text{ Conversion} = \frac{Ao - Af}{Ao} * 100\%,$$

where $A_o$ is the initial number of moles of reactant A; and $A_f$ is the final number of moles of reactant A.

Selectivity is the percentage of product C produced from the converted amount of reactant A, as expressed by the following equation:

$$\text{Selectivity (\%)} = \frac{Cf * \frac{a}{c}}{Ao - Af} * 100\%,$$

where $A_o$ is the starting moles of reactant A; $A_f$ is the final number of moles of reactant A; and $C_f$ is the number of moles of product C. In some embodiments where "a" and "c"=1, and the equation can be simplified to:

$$\text{Selectivity (\%)} = \frac{Cf}{Ao - Af} * 100\%,$$

The yield of product C is the percentage of reactant A that is converted into product C, as expressed by the following equation:

$$\text{Yield (\%)} = \frac{(\text{Conversion} * \text{Selectivity})}{100}$$

In certain embodiments, the methods described herein have a yield of at least 10%, 20%, 30%, 40%, 50%, 60%, 70%, 75%, 80%, 85%, 90%, 95%, or 99% by weight. In other embodiments, the yield is between 10% to 90%, 20% to 80%, 30% to 80%, 40% to 80%, 50%-80%, or 60%-80% by weight.

In certain embodiments, the methods described herein have a selectivity of at least 10%, 20%, 30%, 40%, 50%, 60%, 70%, 80%, 90%, or 99%. In other embodiments, the selectivity is between 40% to 99%, 40% to 95%, 40% to 90%, 40% to 80%, 50% to 99%, 50% to 95%, 50% to 90%, 50% to 80%, 60% to 99%, 60% to 95%, 60% to 90%, 60% to 80%, 70% to 99%, 70% to 95%, 70% to 90%, or 70% to 80%.

In certain embodiments, with reference to FIG. 2, the reaction conditions described herein for producing a compound of formula I (compound 110) reduces the amount of a compound of formula III (compound 202) produced. The amount of byproducts (compound 202) present in the reaction mixture is described relative to the amount of starting materials (compound 102). For example, in one embodiment where a compound of formula I is para-xylene, the reaction conditions described herein reduces the amount of 2,5-hexanedione produced as a byproduct. The amount of 2,5-hexanedione present in the reaction mixture is described relative to DMF used in the reaction. In one embodiment, the reaction mixture has less than 10% of 2,5-hexanedione. In other embodiments, the reaction mixture has less than 5%, 2.5%, 1%, 0.05%, or 0.01% of 2,5-hexanedione. In other embodiments, the reaction mixture has between 1-10%, 1-5%, or 0.01-1% of 2,5-hexanedione.

In some embodiments, a compound of formula I is suitable for manufacture of one or more plastics. In other embodiments, a compound of formula I is suitable for manufacture of one or more fuels. In some embodiments where para-xylene is produced, the methods include further oxidizing the para-xylene to produce terephthalic acid. In other embodiments, the terephthalic acid is further processed to manufacture one or more plastics.

As used herein, the term "about" refers to an approximation of a stated value within an acceptable range. Preferably, the range is +/-10% of the stated value.

EXAMPLES

The following Examples are merely illustrative and are not meant to limit any aspects of the present disclosure in any way.

Example 1

Preparation of Para-Xylene from DMF

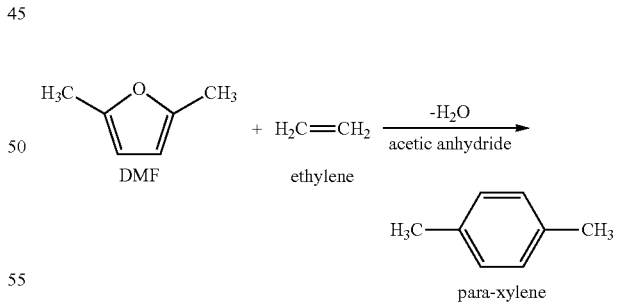

This example demonstrates the conversion of DMF into para-xylene. Dimethylfuran (DMF, 0.25 mL), and acetic anhydride (0.010 mL) were added to a hastelloy reactor (1 L) under an argon atmosphere. An inert compound, such as tetradecane (0.25 mL), was added to the reaction only to serve as an internal standard to quantify the product produced. The reactor was sealed and charged with ethylene gas (50 barg). The reactor was heated (175° C.) and mechanically stirred for 15 hours. The reactor was cooled to room temperature, and vented into a trap containing dichloromethane (DCM, 250 mL). Dichloromethane (100 mL) was used to extract the remaining organics from the reactor.

An aliquot was taken from the DCM trap and from the DCM extraction solution, and analyzed by gas chromatography mass spectrum (GCMS). The following GCMS protocol was used. Initial oven temp: 45° C. for 3 minutes then 15° C./min to 220° C. (14.67 min run time); inlet temperature: 300° C.; column type: HP-5MS 5% phenyl methyl siloxane. A peak at retention time 4.802 was observed, corresponding to para-xylene. A peak at retention time 2.251 was also observed, corresponding to DMF.

Example 2

Effect of Temperature on Synthesis of Para-Xylene from DMF

This example demonstrates the impact of temperature on the synthesis of para-xylene from DMF. Three different catalysts were tested, including $AlCl_3$, $Cu(OTf)_2$ and $CuCl_2$, at various temperature between 150° C. and 220° C.

For each catalyst and temperature set forth in Table 1 below, the following general procedure was used: 2,5-dimethylfuran (10 g, 0.10 mole), 1,4-dioxane (200 g), 4 Å sieves (2 g), and the catalyst set forth in Table 1 below (1 g) were added into a hastelloy autoclave reactor, which was equipped with a gas impeller. The contents in the reactor were stirred at room temperature. The reactor was charged with ethylene gas until the pressure stabilized to 450 psig. The reactor was heated to the temperature as set forth in Table 1 below, and allowed to react for 24 hours. The reactor was then cooled and depressurized. A sample was taken from the reactor, and the sample was analyzed by $^1$H-NMR.

TABLE 1

Effect of temperature on the synthesis of para-xylene from DMF

| Entry | Temperature (° C.) | Catalyst | Conversion (%) | Selectivity (%) | HD (mol %) |
|---|---|---|---|---|---|
| 1 | 150 | $AlCl_3$ | 22 | 40 | 2.9 |
| 2 | 190 | $AlCl_3$ | 73 | 79 | 5.8 |
| 3 | 220 | $AlCl_3$ | 98 | 89 | 3.5 |
| 4 | 190 | $Cu(OTf)_2$ | 68 | 88 | 9.1 |
| 5 | 220 | $Cu(OTf)_2$ | 99 | 96 | 1.8 |
| 6 | 190 | $CuCl_2$ | 64 | 87 | 4.6 |
| 7 | 220 | $CuCl_2$ | 93 | 92 | 3.6 |

Example 3

Effect of Catalyst on Synthesis of Para-Xylene from DMF

This example demonstrates the impact of the catalyst on the synthesis of para-xylene from DMF. Various different Lewis acid were tested.

For each catalyst, temperature, reaction time and pressure of ethylene added set forth in Table 2 below, the following general procedure was used, unless as otherwise noted in Table 2: 2,5-dimethylfuran (10 g, 0.10 mole), 1,4-dioxane (200 g), 4 Å sieves (2 g), and catalyst (1 g) was added into a hastelloy autoclave reactor and was stirred at room temperature. The reactor was charged with ethylene gas until the pressure stabilized to the pressure set forth in Table 2 below. The reactor was heated to the temperature set forth in Table 2 below, and allowed to react for 24 hours. The reactor was then cooled and depressurized. A sample was taken from the reactor, and the sample was analyzed by $^1$H-NMR or GC-FID.

TABLE 2

Effect of catalyst on the synthesis of para-Xylene from DMF

| Entry | Acid | Temperature (° C.) | Reaction time (h) | Ethylene (psig) | Conversion (%) | Selectivity (%) | HD (mole %) |
|---|---|---|---|---|---|---|---|
| 1 | $AlCl_3$ | 220 | 24 | 490 | 98 | 89 | 3.5 |
| 2 | acetic anhydride[a, d] | 225 | 65 | 140 | 42 | 61 | — |
| 3 | acetic acid[a] | 225 | 65 | 780 | 64 | 60 | — |
| 4 | chloroacetic anhydride[a, d] | 225 | 15 | 140 | 19 | 21 | — |
| 5 | chloroacetic acid[a] | 225 | 15 | 140 | 9 | 10 | — |
| 7 | $CuCl_2$ | 220 | 24 | 490 | 92 | 92 | 3.6 |
| 8 | $Cu(OTf)_2$ | 220 | 24 | 490 | 99 | 96 | 1.8 |
| 9 | Cu (II)/Mordenite | 220 | 24 | 490 | 8 | 18 | 6.3 |
| 10 | $CuCl_2$/Alumina[b] | 250 | 7 | 500 | 52 | 70 | 1.3 |
| 11 | $CuCl_2$/HY Zeolite[b] | 250 | 7 | 500 | 77 | 82 | 1.3 |
| 12 | $CoCl_2$ | 190 | 24 | 490 | 40 | 76 | 9.1 |
| 15 | $Gd(OTf)_3$ | 190 | 24 | 490 | 72 | 75 | 2.7 |
| 16 | H-Y-Zeolite | 190 | 24 | 490 | 56 | 49 | 4.6 |
| 17 | $InCl_3$ | 190 | 24 | 490 | 73 | 75 | 1.4 |
| 18 | $In(OTf)_3$ | 190 | 24 | 490 | 79 | 80 | 7.6 |
| 19 | $NiCl_2$ | 190 | 24 | 490 | 10 | 56 | 1 |
| 20 | Norit (steam treated) | 190 | 24 | 490 | 5 | 20 | 1.1 |
| 21 | Norit ($H_3PO_4$ acid treated) | 220 | 24 | 490 | 11 | 73 | 0.9 |
| 23 | $P_2O_5$[c] | 225 | 4 | 260 | 100 | 17 | — |
| 27 | $Y(OTf)_3$ | 250 | 7 | 550 | 97 | 91 | 0 |
| 28 | $ZnCl_2$ | 190 | 24 | 500 | 26 | 79 | 0 |
| 29 | control (no acid catalyst) | 225 | 14 | 500 | 18 | 6 | 0 |

[a] Reaction was performed without a solvent
[b] Reaction was performed without 4 Å sieves
[c] Reaction was performed with hexane as the solvent
[d] Anhydrides were undistilled, and had a small percentage of hydrolyzed anhydride

Example 4

Effect of Catalyst on Synthesis of Para-Xylene from DMF

This example describes experiments testing various additional Lewis acids in the synthesis of para-xylene from DMF. The Lewis acids include Bi(OTf)$_3$, CrCl$_3$, Fe(OTf)$_2$, MnCl$_2$, SnCl$_2$, TiCl$_4$, and VCl$_2$. For each of these catalysts, 2,5-dimethylfuran (10 g, 0.10 mole), 1,4-dioxane (200 g), 4 Å sieves (2 g), and catalyst (1 g) are added into a hastelloy autoclave reactor and are stirred at room temperature. The reactor is charged with ethylene gas until the pressure stabilizes to 500 psig. The reactor is heated to 225° C. The reaction is monitored. Once the reaction reaches a threshold conversion percentage, the reactor is cooled and depressurized. A sample is taken from the reactor, and is analyzed by $^1$H-NMR or GC-FID.

Example 5

Effect of Solvent on Synthesis of Para-Xylene from DMF

This example demonstrates the impact of the solvent on the synthesis of para-xylene from DMF. Five different solvents were tested.

For solvents #1-4 in Table 3 below, the following general procedure was used: 2,5-dimethylfuran (10 g, 0.10 mole), solvent (200 g), and yttrium triflate (0.5 g) were added into a hastelloy autoclave reactor, which was equipped with a gas impeller. The contents of the reactor were stirred at room temperature. The reactor was charged with ethylene gas until the pressure stabilized to 500 psig. The reactor was heated to about 250° C., and allowed to react for 7 hours. The reactor was then cooled and depressurized. A sample was taken from the reactor, and the sample was analyzed by $^1$H-NMR.

For solvent #5 in Table 3 below, the following procedure was used: 2,5-dimethylfuran (44.5 g, 0.46 mole), tetrahydrofuran (250 mL), ethylene (450 psig), calcium sulfate (13.7 g) and aluminum chloride (2.0 g) were added into a hastelloy autoclave reactor. The contents of the reactor were stirred at room temperature. The reactor was charged with ethylene gas until the pressure stabilized to 500 psig. The reactor was heated to about 220° C. and allowed to react for 24 hours. The reactor was then cooled and depressurized. A sample was taken from the reactor, and the sample was analyzed by $^1$H-NMR.

TABLE 3

Effect of solvent on the synthesis of para-xylene from DMF

| Entry | Solvent | Conversion (%) | Selectivity (%) |
|---|---|---|---|
| 1 | 1,4-dioxane | 99 | 84 |
| 2 | tetraethylene glycol | 100 | 27 |
| 3 | sulfolane | 88 | 41 |
| 4 | triglyme | 99 | 81 |
| 5 | tetrahydrofuran | 95 | 71 |

Example 6

Effect of Catalyst Loading on Synthesis of Para-Xylene from DMF

This example demonstrates the impact of the amount of catalyst used on the synthesis of para-xylene from DMF.

For each reaction set forth in Table 4 below, the following general procedure was used: 2,5-dimethylfuran (amount specified in Table 4), dioxane (amount specified in Table 4), and copper triflate (amount specified in Table 4) were added into a hastelloy autoclave reactor, which was equipped with a gas impeller, and was stirred at room temperature. The reactor was charged with ethylene gas until the pressure stabilized to 500 psig. The reactor was heated to 250° C. and allowed to react for 7 hours. The reactor was then cooled and depressurized. A sample was taken from the reactor, and the sample was analyzed by $^1$H-NMR.

TABLE 4

Effect of copper triflate loading on the synthesis of para-xylene from DMF

| Entry | Catalyst (g) | DMF (g) | Dioxane (g) | Conversion (%) | Selectivity (%) | Time to reach 50% conversion (h) |
|---|---|---|---|---|---|---|
| 1 | 0.025 | 5 | 100 | 99 | 100 | 0.3 |
| 2 | 0.10 | 10 | 200 | 100 | 95 | 1.0 |
| 3 | 0.50 | 10 | 200 | 100 | 86 | 1.3 |

Example 7

Synthesis of Toluene from Methylfuran and Ethylene

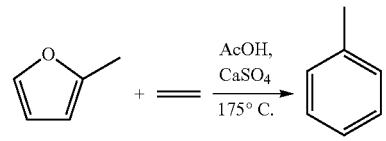

2-Methylfuran (4.113 g, 0.05 mole), calcium sulfate (3.25 g), and acetic acid (1.06 g) was added into a hastelloy autoclave reactor and was stirred at room temperature. The reactor was charged with ethylene gas until the pressure stabilized to 780 psig. The reactor was heated to 175° C. and allowed to react for 65 hours. The reactor was then cooled, depressurized, and the solution was analyzed by GC-FID, GC-MS giving toluene (586.2 mg).

What is claimed:

1. A method for producing para-xylene, comprising:
    combining 2,5-dimethylfuran with ethylene and a catalyst to form a reaction mixture, wherein the catalyst comprises a metal cation and a triflate counterion, and wherein the metal cation is a Group 3 metal cation, a Group 9 metal cation, a Group 10 metal cation, a Group 11 metal cation, or a lanthanide series metal cation; and
    producing para-xylene from at least a portion of the 2,5-dimethylfuran and at least a portion of the ethylene in the reaction mixture.

2. The method of claim 1, further comprising isolating the para-xylene from the reaction mixture.

3. The method of claim 1, wherein the 2,5-dimethylfuran, the ethylene, and the catalyst are further combined with a solvent to form the reaction mixture.

4. The method of claim 3, wherein the solvent has a dipole moment above 0.1.

5. The method of claim 3, wherein the solvent comprises an ether.

6. The method of claim 3, wherein the solvent comprises dioxane, glyme, diglyme, triglyme, tetraglyme, or tetrahydrofuran, or any mixtures thereof.

7. The method of claim 6, wherein the solvent comprises 1,4-dioxane.

8. The method of claim 1, wherein the metal cation is a divalent metal cation or a trivalent metal cation.

9. The method of claim 8, wherein the divalent metal cation is selected from the group consisting of $Zn^{2+}$, $Cu^{2+}$, $Ni^{2+}$, and $Co^{2+}$.

10. The method of claim 8, wherein the trivalent metal cation is selected from the group consisting of $Al^{3+}$, $In^{3+}$, $Fe^{3+}$, $La^{3+}$, $Gd^{3+}$, and $Y^{3+}$.

11. The method of claim 1, wherein the metal cation is silver, lead, or scandium.

12. The method of claim 1, wherein less than 10% of the reaction mixture is 2,5-hexanedione.

13. The method of claim 1, wherein at least a portion of the 2,5-dimethylfuran is converted to para-xylene at a temperature of at least 150° C.

14. The method of claim 13, wherein at least a portion of the 2,5-dimethylfuran is converted to para-xylene at a temperature of between 150° C. and 300° C.

15. The method of claim 1, further comprising adding one or more molecular sieves to the reaction mixture.

16. The method of claim 15, wherein the one or more molecular sieves has a pore size of 3 Å to 100 Å.

17. The method of claim 3, wherein the solvent comprises a $C_1$ to $C_{10}$ aliphatic solvent, a $C_6$ to $C_{12}$ aromatic solvent, or any combinations thereof.

18. The method of claim 3, wherein the solvent comprises a $C_6$-$C_{12}$ aromatic solvent.

19. The method of claim 18, wherein the solvent comprises toluene.

20. The method of claim 1, wherein the catalyst is a water-stable acid catalyst.

21. The method of claim 1, wherein the metal cation is a Group 3 metal cation.

22. The method of claim 1, wherein the metal cation is a Group 11 metal cation.

23. The method of claim 1, wherein the metal cation is a lanthanide series metal cation.

24. A method for producing terephthalic acid, comprising:
a) producing para-xylene according to the method of claim 1; and
b) oxidizing the para-xylene to produce terephthalic acid.

25. A method for producing a compound of formula I, wherein formula I has the structure:

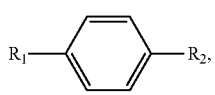

(formula I)

wherein each $R_1$ and $R_2$ is independently hydrogen or alkyl, wherein the method comprises:
combining a compound of formula II with ethylene and a catalyst to form a reaction mixture,
wherein the compound of formula II is:

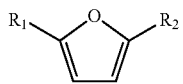

(II)

wherein $R_1$ and $R_2$ are as defined for formula I above, and
wherein the catalyst comprises a metal cation and a triflate counterion, and wherein the metal cation is a Group 3 metal cation, a Group 9 metal cation, a Group 10 metal cation, a Group 11 metal cation, or a lanthanide series metal cation; and
producing a compound of formula I from at least a portion of the compound of formula II and at least a portion of the ethylene in the reaction mixture.

26. The method of claim 25, wherein $R_1$ and $R_2$ are each methyl.

27. The method of claim 25, wherein $R_1$ is H and $R_2$ is methyl.

28. The method of claim 25, wherein at least a portion of the 2,5-dimethylfuran is converted to para-xylene at a temperature of at least 150° C.

29. The method of claim 25, further comprising adding one or more molecular sieves to the reaction mixture.

30. The method of claim 25, wherein less than 10% of the reaction mixture is a compound of formula III, wherein formula III has the structure

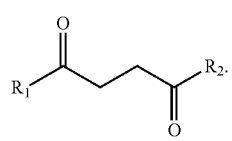

(formula III)

31. The method of claim 25, wherein the metal cation is silver, lead, or scandium.

32. The method of claim 25, wherein the compound of formula II, the ethylene, and the catalyst are further combined with a solvent to form the reaction mixture.

33. The method of claim 32, wherein the solvent comprises a $C_6$-$C_{12}$ aromatic solvent.

34. The method of claim 33, wherein the solvent comprises toluene.

35. The method of claim 25, wherein the catalyst is a water-stable acid catalyst.

36. The method of claim 25, wherein the metal cation is a Group 3 metal cation.

37. The method of claim 25, wherein the metal cation is a Group 11 metal cation.

38. The method of claim 25, wherein the metal cation is a lanthanide series metal cation.

39. The method of claim 32, wherein the solvent has a dipole moment above 0.1.

40. The method of claim 32, wherein the solvent comprises an ether.

41. The method of claim 32, wherein the solvent comprises dioxane, tetrahydrofuran, triglyme, or sulfolane, or any combinations thereof.

42. The method of claim 41, wherein the solvent comprises 1,4-dioxane.

43. The method of claim 3, wherein the metal cation is a trivalent metal cation selected from the group consisting of $Al^{3+}$, $In^{3+}$, $Fe^{3+}$, $La^{3+}$, $Gd^{3+}$, and $Y^{3+}$.

44. The method of claim 3, wherein the metal cation is silver, lead, or scandium.

* * * * *